(12) United States Patent
Suzui et al.

(10) Patent No.: US 12,347,103 B2
(45) Date of Patent: Jul. 1, 2025

(54) LEARNING APPARATUS, LEARNING SYSTEM, LEARNING METHOD OF MACHINE LEARNING MODEL, AND STORAGE MEDIUM

(71) Applicant: Konica Minolta, Inc., Tokyo (JP)

(72) Inventors: Eri Suzui, Hino (JP); Hitoshi Futamura, Hachioji (JP); Shinsuke Katsuhara, Kodaira (JP); Hirotake Minami, Fuchu (JP); Nodoka Iida, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 309 days.

(21) Appl. No.: 17/806,165

(22) Filed: Jun. 9, 2022

(65) Prior Publication Data

US 2022/0405924 A1  Dec. 22, 2022

(30) Foreign Application Priority Data

Jun. 21, 2021  (JP) .................................. 2021-102146

(51) Int. Cl.
*G06T 7/00* (2017.01)
*G16H 30/40* (2018.01)

(52) U.S. Cl.
CPC .......... *G06T 7/0012* (2013.01); *G16H 30/40* (2018.01); *G06T 2207/10081* (2013.01); *G06T 2207/10088* (2013.01); *G06T 2207/10104* (2013.01); *G06T 2207/10116* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| 2018/0336677 | A1* | 11/2018 | Sloan | G06T 7/0012 |
| 2020/0184639 | A1* | 6/2020 | Park | G06T 11/003 |
| 2020/0193285 | A1* | 6/2020 | Ishii | G06N 3/084 |

(Continued)

FOREIGN PATENT DOCUMENTS

| CN | 111798410 | A | * | 10/2020 | | |
| CN | 112465694 | A | * | 3/2021 | ............. | G02B 27/00 |
| CN | 110222705 | B | * | 10/2023 | ........... | G06F 18/214 |

(Continued)

OTHER PUBLICATIONS

Office Action, dated Feb. 4, 2025, issued for the corresponding Japanese Patent Application No. 2021-102146, 7 pages, with English translation.

(Continued)

*Primary Examiner* — Mohammed Rachedine
(74) *Attorney, Agent, or Firm* — LUCAS & MERCANTI, LLP

(57) ABSTRACT

A learning apparatus includes a hardware processor. The hardware processor obtains a first medical image. The hardware processor generates a second medical image in which a feature according to feature information related to a portion other than a recognition target of the first medical image is made close to the feature according to standard feature information which is to be a predetermined standard. The second medical image is used to train a machine learning model.

14 Claims, 4 Drawing Sheets

(56) References Cited

U.S. PATENT DOCUMENTS

2020/0335197 A1* 10/2020 Hong ..................... G16H 30/40
2021/0248736 A1*  8/2021 Kamen ................. G06F 18/214

FOREIGN PATENT DOCUMENTS

JP    2021-194261 A    12/2021
WO    2018/167900 A1    9/2018

OTHER PUBLICATIONS

Office Action, dated Apr. 30, 2025, which was issued for the corresponding Japanese Patent Application No. 2021-102146, 6 pages, with English translation.

* cited by examiner

LEARNING APPARATUS, LEARNING SYSTEM, LEARNING METHOD OF MACHINE LEARNING MODEL, AND STORAGE MEDIUM

CROSS-REFERENCE TO RELATED APPLICATIONS

The entire disclosure of Japanese Patent Application No. 2021-102146 filed on Jun. 21, 2021 is incorporated herein by reference in its entirety.

BACKGROUND

Technological Field

The present invention relates to a learning apparatus, a learning system, a learning method of a machine learning model and a storage medium.

Description of the Related Art

Conventionally, diagnosis is widely performed by detecting and recognizing lesions and abnormal locations related to diseases from a medical image. However, if physicians and technicians individually view the image and detect and recognize the lesions, it is time-consuming. Moreover, such method relies on the skill of each individual physician, and the physician may overlook lesions.

Meanwhile, research, development, and use of image recognition technology using electronic computers are expanding. As one of the image recognition technologies, there is a well-known machine learning model that uses convolutional neural networks, etc. Such machine learning model is used to learn to be able to discriminate a recognition target based on a large amount of image data that may or may not include the recognition target in advance. However, when the image data for learning is insufficient, sensitivity develops for differences in portions other than the original recognition target. This causes problems such as incorrect diagnoses being obtained. When the machine learning model is used for specialized purposes such as medical images, images including the recognition target such as lesions cannot always be sufficiently obtained.

WO 2018/167900 describes a technique to generate adversarial features in a subspace that contributes to learning in a multidimensional space regarding the features in order to better optimize a threshold used in determination.

SUMMARY

However, according to the conventional technique, the data including the data in the dimension that does not contribute to learning is added and the amount of learning is increased. Therefore, there is a problem such as learning efficiency not always being good.

The purpose of the present invention is to provide a learning apparatus, a learning system, a learning method of a machine learning model and a storage medium in order to train a machine learning model more appropriately with less data.

To achieve at least abovementioned objects, according to an aspect of the present invention, a learning apparatus reflecting one aspect of the present invention includes, a hardware processor, wherein the hardware processor obtains a first medical image, wherein the hardware processor generates a second medical image in which a feature according to feature information related to a portion other than a recognition target of the first medical image is made close to the feature according to standard feature information which is to be a predetermined standard, and wherein the second medical image is used to train a machine learning model.

According to another aspect, a learning system includes: a hardware processor, wherein the hardware processor obtains a first medical image, wherein the hardware processor generates a second medical image in which a feature according to feature information related to a portion other than a recognition target of the first medical image is made close to the feature according to standard feature information which is to be a predetermined standard, and wherein the hardware processor uses the second medical image to train a machine learning model.

According to another aspect, a learning method of a machine learning model includes: obtaining a first medical image; generating a second medical image in which a feature according to feature information related to a portion other than a recognition target of the first medical image is made close to the feature according to standard feature information which is to be a predetermined standard, and training a machine learning model using the second medical image.

According to another aspect, a non-transitory computer-readable storage medium storing a program causing a computer to perform: obtaining a first medical image; generating a second medical image in which a feature according to feature information related to a portion other than a recognition target of the first medical image is made close to the feature according to standard feature information which is to be a predetermined standard, and training a machine learning model using the second medical image.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, embodiments of the present invention are described with reference to the drawings.

However, the scope of the invention is not limited to the disclosed embodiments.

Figure 1:
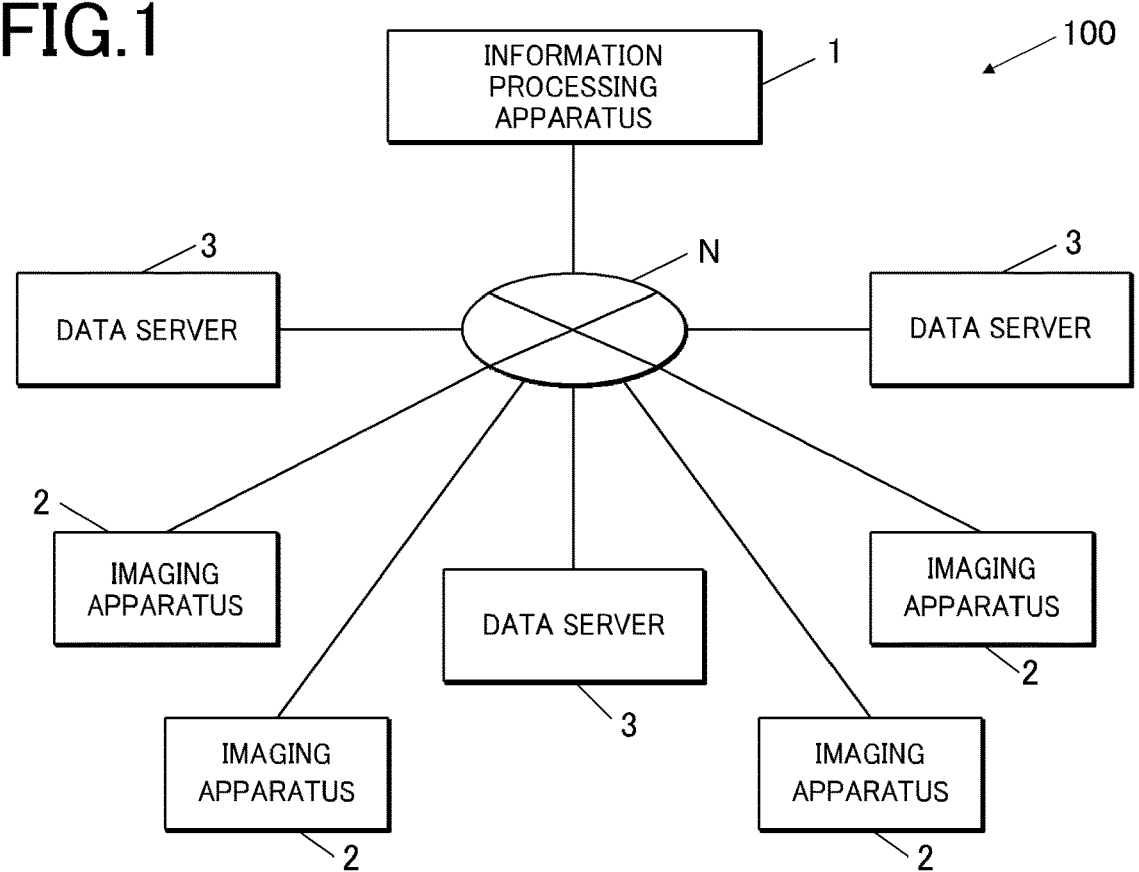
FIG. 1 is a diagram schematically describing an overall structure of an information system according to the present embodiment.

FIG. 1 is a diagram schematically describing an overall structure of an information system 100 according to the present embodiment.

The information system 100 includes an information processing apparatus 1, an imaging apparatus 2 connected through a communication network N to be able to transmit and receive data to and from the information processing apparatus 1, and a data server 3. The communication network N may be within a specific LAN (Local Area Network) or a VPN (Virtual Private Network). Alternatively, the communication network N may be a connection through the Internet (including connection in which authentication is not required).

The information processing apparatus 1 is a learning apparatus according to the present embodiment and generates a machine learning model to perform diagnosis of an image based on obtained imaged image data.

The imaging apparatus 2 is a modality that images an image for medical purposes and generates and outputs the imaged image. That is, here, the imaged image is a medical image, and an imaged range includes a diagnosis target site such as an injury or disease in a human body. Although not limited, the type of imaging apparatus 2 may be any of the following, for example, X-ray imaging apparatus, ultrasound imaging apparatus, nuclear magnetic resonance imaging apparatus (MRI), positron emission tomography imaging apparatus (PET), and the like (that is, the imaged medical image is an X-ray imaged image, an ultrasound imaged image, a nuclear magnetic resonance imaged image, a positron emission tomography imaged image, etc.). The X-ray imaging apparatus may include an imaging apparatus that generates digital data related to simple imaging such as CR or DR, and an imaging apparatus related to CT (computed tomography). A plurality of imaging apparatuses 2 connected to the communication network N may be provided, and the plurality of imaging apparatuses 2 may include a plurality of different types of imaging apparatuses or a plurality of the same type of imaging apparatus. The plurality of the same type of imaging apparatus may be a same model from a same manufacturer, apparatuses from different manufacturers, or different models from the same manufacturer.

The data server 3 stores imaged image data imaged by the imaging apparatus 2 and imaging information related to the imaged image data, and diagnosis information of the patient associated with the imaged image. A plurality of data servers 3 may be provided. The data server 3 may correspond one to one to the imaging apparatus 2 or may collect the image data of the plurality of imaging apparatuses 2. The imaging apparatus 2 does not have to be configured to enable direct access from the information processing apparatus 1 through the communication network N. The imaged image data may be first obtained and held in the data server 3 and then obtained by the information processing apparatus 1 by communication between the data server 3 and the information processing apparatus 1.

First Embodiment

Figure 2:
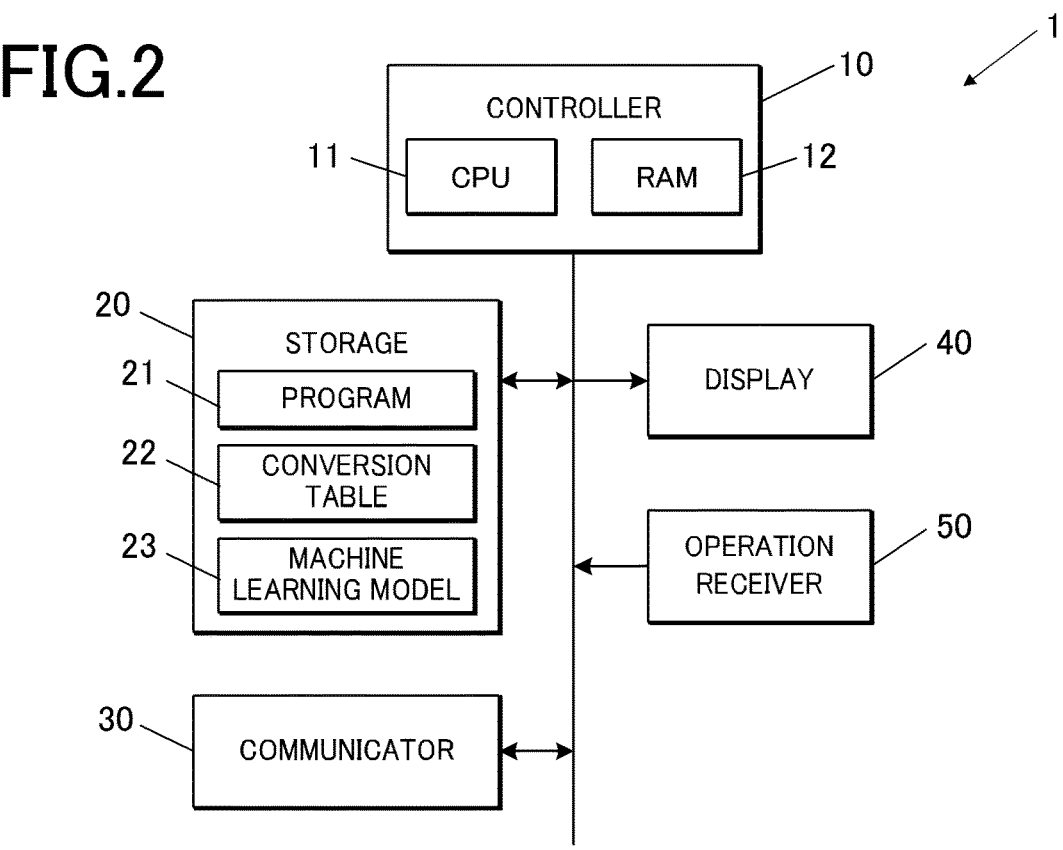
FIG. 2 is a block diagram showing a functional configuration of an information processing apparatus according to a first embodiment.

FIG. 2 is a block diagram showing a functional configuration of the information processing apparatus 1 according to the first embodiment.

For example, the information processing apparatus 1 is a normal computer (PC), and includes, for example, a controller 10 (hardware processor, obtainer, image generator, learner), a storage 20, a communicator 30, a display 40, and an operation receiver 50.

The controller 10 centrally controls the operation of the information processing apparatus 1. The controller 10 includes a CPU (Central Processing Unit) 11 and a RAM (Random Access Memory) 12. The CPU 11 is a hardware processor that performs various arithmetic processes. The RAM 12 provides a working memory space for the CPU 11 and stores temporary data. The temporary data includes deployment data and setting data for a control program, and the CPU 11 executes contents of the program based on the deployed data. The CPU 11 does not have to be a single CPU, and a plurality of CPUs 11 can perform the same process or the plurality of processes can be performed in parallel. The controller 10 may include a hardware logic circuit dedicated to specific processes in addition to the CPU 11. The RAM 12 may include a separate memory for work of the CPU 11 and a memory for storing various data, or a common memory may be dynamically allocated to each process as necessary.

The storage 20 stores and holds the above program 21 for control, machine learning model 23, and setting data. The storage 20 is able to store obtained medical image data and a conversion table 22 (conversion contents) which is conversion data. The storage 20 includes a non-volatile memory such as but not limited to a flash memory. The storage 20 is not limited to being provided in the information processing apparatus 1 and may include an external auxiliary storage device. The auxiliary storage device may be located on a network as a cloud server or the like.

The program 21 includes a control process program for training the machine learning model 23. The machine learning model 23 is the initial data of a machine learning model (learned model) learned to output recognition results of lesions and other medically abnormal locations in response to input of medical image data. The algorithm of the machine learning model 23 is not limited as long as the image can be recognized. As a method of mechanical learning suitable for image recognition, for example, deep learning using a convolutional neural network is widely used. For example, semantic segmentation can be used for identification and recognition of lesion locations.

The conversion table 22 is data that stores conversion contents to convert and generate medical image data (second medical image data) input to the mechanical learning model 23 from the original medical image data (first medical image data). The data is stored associated with later described feature information related to the original medical image data. The conversion table 22 is described later.

The storage 20 may include a volatile memory for temporarily storing a large amount of medical image data. Alternatively, the medical image data and its processed data may be stored in a nonvolatile memory similar to programs. The nonvolatile memory may include a HDD (Hard Disk Drive), and may also include a flash memory in addition to or instead of the HDD.

The communicator 30 controls data communication performed between external devices through the communication network N, etc. For example, the communicator 30 may include a network card that controls communication based on a communication standard (TCP/IP, etc.) regarding communication using a LAN. The communication is not limited to wired communication such as a LAN, and the communicator 30 may include a network card that performs control to enable wireless control by WiFi, etc. The communicator 30 may include a driver to read data of a portable storage medium such as a CDR, or a driver to perform communication directly with external devices such as a USB (Universal Serial Bus).

The display 40 includes a display screen and performs display based on control by the controller 10. The display screen includes a digital display screen such as a liquid crystal display (LCD) and may display a status related to the control operation by the controller 10 or a menu in order to receive input according to operation by the user. The display screen may be able to display the image displayed by image data as described later. The display 40 may include an image forming apparatus (printer) that forms an image of the displayed contents.

The operation receiver 50 receives operation from outside such as a user, generates an operation signal according to the received operation type, and outputs the operation signal to the controller 10. The operation receiver 50 may include a press button switch, a slide switch, a lock switch and the like that are switch buttons to receive physical switching operations, and an input device such as various keyboards and/or a pointing device such as a mouse. In addition to or instead of the above, the operation receiver 50 may include a touch panel. The touch panel is positioned overlapped with the display screen of the display 40, and an operation signal showing a touched position or a continuous state of the touch operation as the operation type is output. With this, the controller 10 is able to specify the contents of the received operation linked with the contents displayed on the display screen.

The information processing apparatus as the computer of the present embodiments includes a controller 10 as the minimum configuration and is at least able to obtain a first medical image.

Next, the features of the medical image are described.

The medical image (first medical image) that is an image imaged by the imaging apparatus 2 is an image imaging a specific site for medical diagnosis as described above with an imaging apparatus suitable for imaging the site or an image in which primary processing is performed on the above-described imaged image. The primary process may include a process that overlaps (combines) or obtains a difference of imaging results of the same site by a plurality of imaging apparatuses 2 or imaging results at different timing by the same imaging apparatus 2. For example, image data in which processing by overlapping and fusing a CT image and a PET image is performed can be used as the data of the medical image.

Even in medical images that image the same subject with the same type of imaging apparatus, the image quality includes unique features related to parameters regarding the imaging information such as manufacturer, model, and equipment of the imaging apparatus. Such features are mainly features related to the image quality such as differences in amount and characteristics of noise, resolution, sharpness, contrast, density and tone. Even if the apparatuses that are the same model are used, the differences in the image quality as described above occur depending on the imaging conditions. The imaging conditions may differ depending on the setting by an operator, skill of the operator, conditions of an imaging room, and the like. When the primary processing is performed on the medical image data, the variation in the image quality may occur depending on the contents of the process (characteristics such as the algorithm or parameters). The image obtaining information that may influence differences in such features (imaging information, imaging conditions, primary processing information) are held with meta data (additional information) such as data of the medical image added or associated. Therefore, by specifying (corresponding) the relation of correspondence between the image obtaining information and the features related to the image quality in advance, the features according to the image obtaining information related to the medical image data can be assumed without analyzing the medical image data itself each time.

Here, although not limited, in order to perform training of the machine learning model 23 as supervised training, the metadata includes information of the medically abnormal locations (that is, recognition target portions recognized in a medical image by a learned model obtained by training with the machine learning model 23) in the medical image as teacher data. Such teacher data may be added before machine learning after the later-described medical image conversion process is performed.

Figure 3:
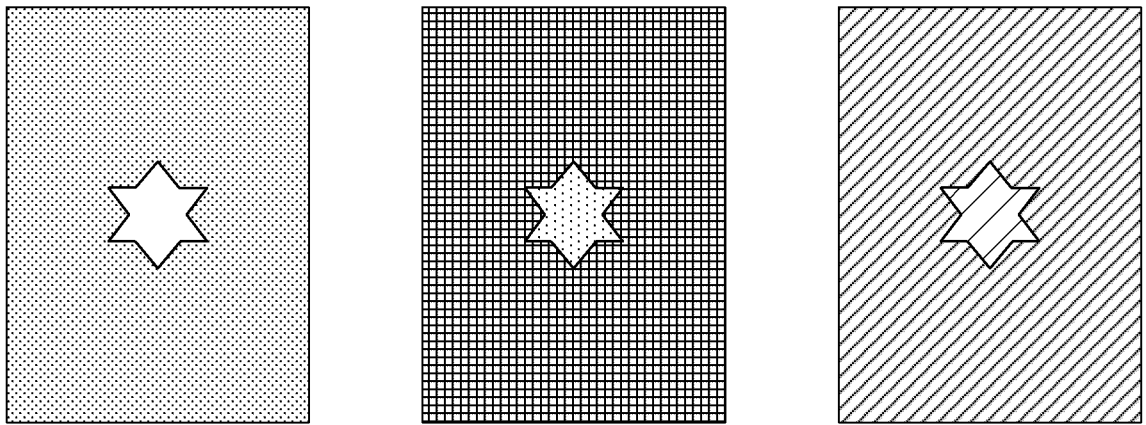
FIG. 3 is a diagram schematically describing a difference related to a portion other than a recognition target.

FIG. 3 is a diagram schematically describing the difference regarding the portion other than the recognition target.

The medical image includes features such as noise amount, noise pattern, and the tone according to the noise with relation to the surroundings (background portion) of the recognition target portion (here, shown in the center in a star shape). Such features are seen in the characteristics of the tone of the recognition target. The features that change due to factors not related to the recognition target (regarding portions other than the recognition target outside the range of the recognition target in the learned model) tend to depend on image obtaining information including parameters such as manufacturer or type of imaging apparatus, model of imaging apparatus, uniqueness of each imaging apparatus, imaging location (facility information), operator (imaging condition) and the like (manufacturer information, type information, model information, imaging condition information, imaging facility information). That is, these are basically specified by referring to image obtaining information.

When a wide range is imaged compared to the diagnostic target, the diagnostic target (imaging target, region of interest ROI) in the images may be cut out to obtain the image when the diagnosis is performed. As the training data, the setting to cut out the target together with other images can be set regardless of the actual ROI (imaging target information). When the cutout is performed, as a result, the resolution and the sharpness of the cutout portion tend to become smaller (lower) than the resolution and the sharpness when the cutout portion is imaged in a state focused from the beginning.

Even if these features are not related to expression of characteristic sites due to a lesion in the recognition target, when many features are detected linked with the recognition target, if the data for learning is not enough, training may be performed incorrectly by learning that the features are related to the recognition target. Specifically, when the learned model is used, as shown in FIG. 3, even if the abnormal location with the same size and same shape is imaged, depending on the imaging condition (specifically, in medical image data including features that are not learned yet and that are from other image quality) the abnormality may be diagnosed as symptoms of a different degree, that is, lighter than the actual state, or characteristic lesions may not be recognized as a pattern and may be overlooked. Such possibilities of problems occurring need to be reduced as much as possible. According to the present embodiment, an image (second medical image) is generated from the original medical image (first medical image) so that such features that are not directly related to the recognition target (related to the portion other than the recognition target), that is, the features that are not useful for training shown in the image are shown with the differences in the features in the image being small. The generated medical image data is used in the training. With this, even if the amount of data for training is small, the training of the features of the image portion of the recognition target can be done more appropriately.

The features which are not useful for machine learning and which are according to the image obtaining information such as the imaging information and the primary processing information are specified as the difference from the feature which is to be a predetermined standard in advance (feature according to the standard feature information). The amount of conversion of the image according to such difference is stored associated with the image obtaining information in the storage 20 as a conversion table 22 (conversion contents). The above are obtained based on the image obtaining information. With this, processing can be performed so that the features that are not useful for recognizing the recognition target in the medical image can easily be made closer to features according to the standard feature information.

The standard feature information is determined from average features of the imaged image obtained in the basic setting of one or a plurality of models of imaging apparatuses 2 that have a large market share. The determination of the conversion amount to make the feature of the medical image according to various image obtaining information closer to the feature regarding the standard feature information can be performed by determining a process in which the degree of similarity becomes higher based on the degree of similarity (the percentage of the similarity of the image being evaluated quantitatively) between the medical image and the standard image including the features according to the standard feature information (feature that is to be the standard), for example. For example, the features of the image data are shown as multidimensional feature vectors, and a cosine similarity degree among the feature vectors or the similarity of Euclidean distance is used as the degree of similarity. With this, the conversion amount (conversion contents) is determined so that the degree of similarity becomes high. Here, although the feature vectors are not limited, an array of intermediate feature amounts obtained from the well-known image recognition techniques such as convolutional neural networks (CNN) can be used.

Alternatively, instead of using the feature vectors, the medical image data can be directly compared with the standard image data according to the standard feature information, and the similarity degree showing how similar the pixel value (brightness value) array and distribution (histogram) is can be calculated.

Alternatively, instead of using the similarity degree as a scalar value, each of the above features regarding the image quality is quantitatively evaluated (may include well-known values such as S/N ratio), and the evaluation value may be converted to become closer to the standard evaluation value regarding the standard feature information.

In the above described feature vectors, at least one conversion amount among the characteristic components regarding the portion other than the recognition portion in the medical image according to the feature information is determined to become closer to the amount of the characteristic component of the corresponding standard feature information (the degree of similarity as a total is increased). More preferably such at least one conversion amount among the characteristic components is determined to match with at least one parameter among the feature information. Here, the conversion amount needs to be determined so that unnecessary conversion is not performed in the areas of the original image portion of the recognition target. The determined conversion amount is stored in the storage 20 as the conversion table 22 associated with the feature information (image obtaining information) of the imaged image data of the conversion target.

The feature information includes a plurality of types of parameters regarding the image obtaining information as described above. Alternatively, a conversion amount can be determined for each variable that can be set for each parameter, and the conversion amount of a plurality of parameters can be calculated and added. Alternatively, the conversion amount can be set for each combination of a plurality of parameters. In such cases, the entire conversion amount can be determined so that the degree of similarity increases in the end.

Among the above image obtaining information, the portion relying on imaging information and the portion relying on each imaging condition and the condition of the primary processing can be adjusted separately. That is, when the image quality is adjusted in the imaging of each image and the primary processing (for example, contrast, tone, density, sharpness, resolution, etc.), if the information of the image quality (image quality information) is included in the metadata, the processing to adjust the conversion amount according to the difference from the image quality set in the image obtaining information can be performed. In the case of a medical image in which adjustment not including the metadata is performed, the difference between the medical image and the standard image is analyzed. If the difference does not match with the conversion amount within the standard range, another process to calculate the conversion amount is performed or the certain imaged image is simply deleted from the medical image for training.

Figure 4:
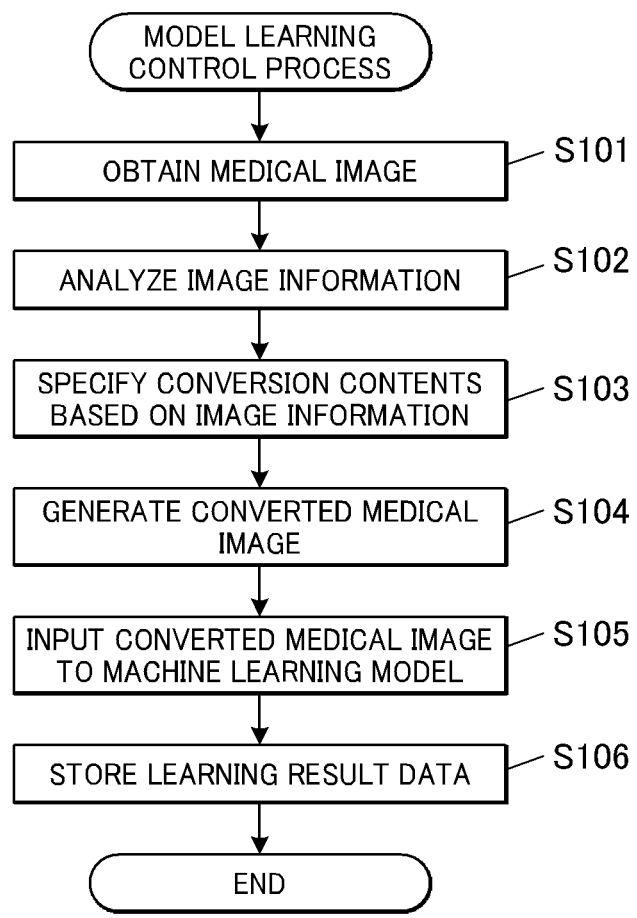
FIG. 4 is a flowchart showing a control procedure of a model learning control process performed in an information processing apparatus according to the first embodiment.

FIG. 4 is a flowchart showing a control procedure by the controller 10 (CPU 11) in a model learning control process performed in the information processing apparatus 1 according to the present embodiment.

The model learning control process as the embodiment of the training method of the machine learning model is started by receiving a predetermined input operation by the user on the operation receiver and obtaining the start instruction through the communicator, for example.

When the model learning control process is started, the controller 10 (CPU 11) obtains the medical image data from outside through the communication network N (step S101; process as obtainer, obtaining step, obtainer). The obtained medical image data is stored in the storage 20, but the storage 20 may be provided externally or located on a network as described above. The controller 10 analyzes the image information of the medical image (including simply referring to the metadata) and obtains the feature information regarding the generating of the conversion image (specifically, image obtaining information) (step S102).

The controller 10 refers to the conversion table 22, obtains the conversion contents (conversion amount) based on the obtained feature information, and determines the conversion contents (step S103). The controller 10 generates the medical image data converting the original medical image data based on the conversion contents (step S104; process as image generator, image generating step, image generator).

When the process to generate the medical image data converted from all of the obtained medical image data ends (as described above, the generating of the medical image data regarding the medical image data that is not suitably converted may be terminated), the controller 10 inputs the generated medical image data in order in the machine learning model 23 to train the machine learning model 23

(step S105; process as learner, learning step, learner). Although the method of learning is not limited, the training is performed by feedback of the difference between the teacher data showing the lesion range included in the medical image data as additional information and the output result of the machine learning model 23.

After the input of all of the medical image data ends, and the learning is completed, the controller 10 stores the data including the setting such as the parameters related to the learned model in the storage 20 (step S106). Then, the controller 10 ends the model learning control process.

Figure 5:
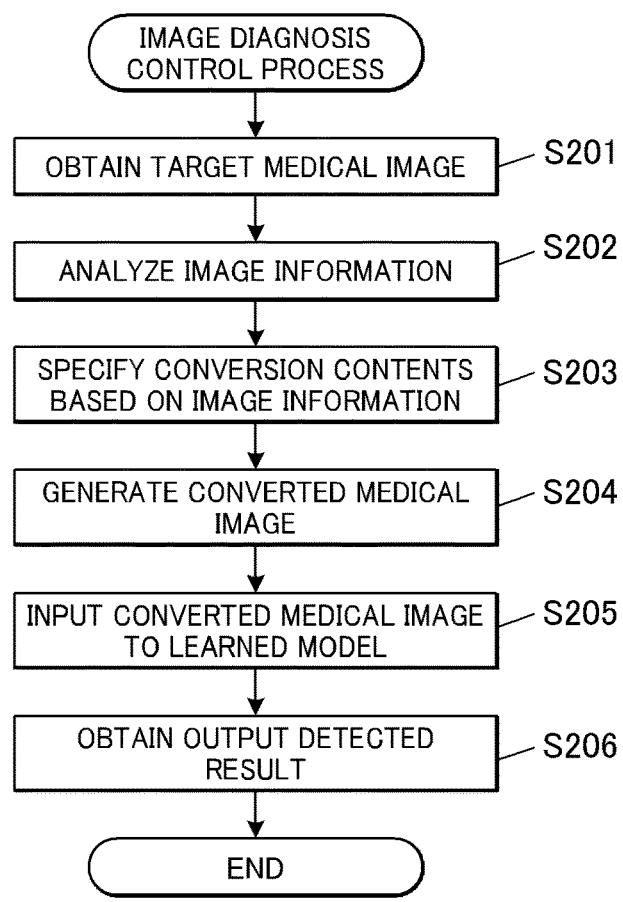
FIG. 5 is a flowchart showing a control procedure of an image diagnosis control process by an obtained learned model.

FIG. 5 is a flowchart showing the control procedure of the image diagnosis control process by the learned model obtained according to the above. The image diagnosis control process may be performed by a controller in any information processing apparatus (PC, etc.) which is separate from the above-described information processing apparatus 1 and in which the learned model and the conversion table 22 is installed. The information processing apparatus that performs recognition of abnormality from the medical image by the learned model is connected to the communication network N and can access to the data server 3.

When the image diagnosis control process starts, the controller obtains the medical image data of the recognition target (step S201). The controller analyzes the image information (mainly image obtaining information) of the medical image data and obtains the feature information of the medical image data (step S202).

The controller specifies the conversion contents of the image so that the feature information becomes close to the standard feature information (step S203). The controller generates the medical image data converted from the original medical image data according to the specified conversion contents (step S204).

The controller inputs the generated medical image data in the learned model (step S205). The controller obtains the recognition result output from the learned model (step S206). If necessary, the controller may output the obtained recognition result as is and/or generate document data and image data based on the recognition result, and output to the data server 3 or display on the display screen the above together with the identification information to be able to specify the original medical image data. Then, the controller ends the image diagnosis control process. The medical image data generated to be input to the learned model can be deleted after obtaining the recognition result.

That is, when the image diagnosis by the learned model according to the present embodiment is performed, the imaged image data that is the target of diagnosis does not have to be input in the learned model as is. The appropriate recognition result can be obtained by converting the imaged image data to image data closer to the standard feature information similar to when the learned model is generated, and then inputting the converted image data. However, even if the medical image data including the recognition target site is input in the learned model without performing the above conversion, if the training is performed so as not to be sensitive to the portion other than the recognition target, a valid diagnosis result can be obtained. Therefore, the present embodiment is not necessarily limited to input of medical image data after conversion.

Second Embodiment

Next, the information processing apparatus 1*a* which is the learning apparatus according to the second embodiment is described.

Figure 6:
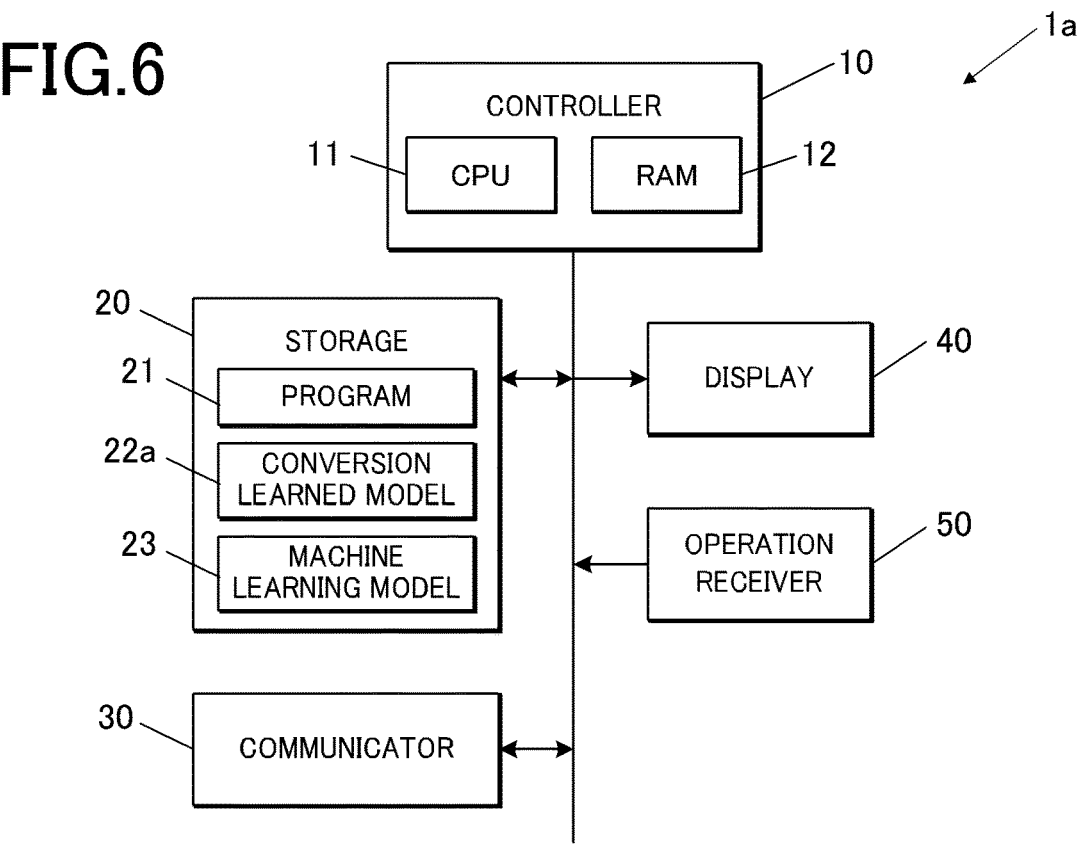
FIG. 6 is a block diagram showing a functional configuration of an information processing apparatus according to a second embodiment.

FIG. 6 is a block diagram showing a functional configuration of the information processing apparatus 1*a* according to the second embodiment.

Compared to the information processing apparatus 1 according to the first embodiment, the difference is that the information processing apparatus 1*a* stores the conversion learned model 22*a* (learned model) instead of the conversion table 22 in the storage 20. The other structures are the same in the first embodiment and the second embodiment. The same reference numerals are applied to the same structures and the description is omitted.

In the information processing apparatus according to the first embodiment, conversion processing is performed using the degree of similarity so that the features of the image are made closer. In the information processing apparatus 1*a* according to the present embodiment, the conversion learned model 22*a* trained by machine learning is used in the conversion process. That is, by inputting the medical image data in such conversion learned model 22*a*, the medical image data close to the feature according to the standard feature information is generated and output.

For example, an adversarial generated network (GAN) can be used as the machine learning algorithm of the conversion learned model 22*a* used in the conversion processing. The imaged image including the difference regarding the portion other than the recognition target is set and input in advance to be learned by the machine learning model. The learning can be performed so that the converted and generated medical image is discriminated from the standard image (true) according to the standard feature information (for example, output 1 (true) in a binary discriminator), that is, to make the difference of the feature related to the standard feature information to be minimum from the feature in the portion not contributing to specifying the diagnosis target, such as the background of the converted and generated medical image.

Figure 7:
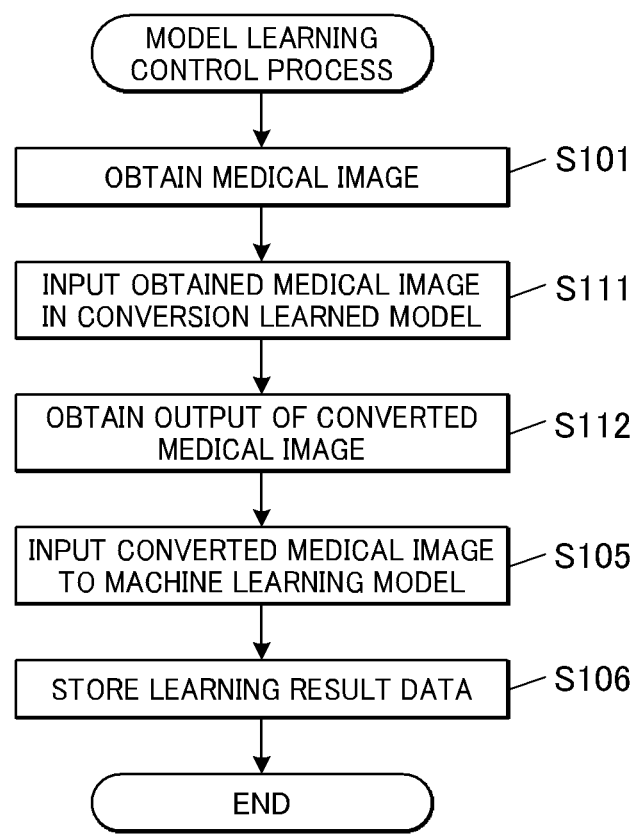
FIG. 7 is a flowchart showing a control procedure of a model learning control process performed in the information processing apparatus according to the second embodiment.

FIG. 7 is a flowchart showing the control procedure by the controller 10 in the model learning control process performed by the information processing apparatus 1*a* according to the second embodiment.

In such model learning control process, the processes in steps S102 to S104 in the model learning control process according to the first embodiment is replaced with the processes described in steps S111 and 112. The other processes are the same. The same reference numerals are applied to the same processing contents and the detailed description is omitted.

After step S101, the controller 10 (CPU 11) inputs the obtained medical image in the conversion learned model 22*a* (step S111). Such conversion learned model 22*a* is the learned model that is trained using the above-described GAN, etc. The controller 10 obtains medical image data generated and output from the conversion learned model 22*a* (step S112). Here, the controller 10 may display the obtained medical image on the display 40, and the user may confirm whether the conversion is performed correctly. The controller 10 may keep the converted medical image for which the operation of approval is accepted on the operation receiver 50, and delete the medical image for which the operation of approval is not received (operation of rejection is received). Then, the process of the controller 10 proceeds to step S105.

As described above, the information processing apparatus 1 according to the learning apparatus of the present embodiment includes a controller 10 (CPU 11). As the obtainer, the controller 10 obtains the first medical image. As the image generator, the controller 10 generates the second medical image in which the feature according to the feature information regarding the portion other than the recognition target in the first medical image is made closer to the feature according to the standard feature information which is to be the predetermined standard. As the learner, the second medical image is used to perform the training of the machine learning model 23 that outputs the recognition result of the recognition target.

As described above, in the information processing apparatus 1, the image quality related to the portion other than the recognition target which is not the range of the recognition target recognized by the learned machine learning model 23 in the second medical image is unified and the learning of the machine learning model 23 is performed. With this, it is possible to prevent the systematic variations in the image quality due to influence from the imaging and primary processing being used in the learning and resulting in useless recognition of the medical abnormal locations and erroneous determination. Moreover, it is possible to obtain a learned model that is able to more appropriately recognize the abnormal locations even if sufficient learning image data is not obtained.

The feature information includes image obtaining information including at least one among manufacturer information of the imaging apparatus 2 of the first medical image, the type information of the imaging apparatus 2, model information, imaging condition information, imaging facility information, and imaging target information. The above generate features that are not random but systematic in the image quality such as noise. Therefore, when learning is performed with an insufficient amount of learning image data, the recognition and learning is incomplete. Depending on the degree of variation in the features of the image quality, it is not possible to accurately recognize the abnormal locations. Therefore, by performing the preprocessing to reduce the systematic difference according to the image obtaining information, and performing machine learning related to recognition of the abnormal locations, it is possible to obtain the trained model that recognizes the abnormal locations more correctly.

The image obtaining information is associated with the feature related to the image quality including at least one of the sharpness, contrast, noise, density, tone and resolution. As described above, the image quality can be unified by the conversion of the features in the image according to the image obtaining information. Therefore, the abnormal locations can be recognized more accurately.

The first medical image is any one of or a combination of two or more of the following, the X-ray imaged image, the ultrasound imaged image, the nuclear magnetic resonance imaged image, and the positron emission tomographic image. When diagnosis is performed with the medical image by imaging a two-dimensional image, there are only a few examples of images with specific symptoms. Therefore, it is difficult to perform accurate recognition excluding small differences related to image quality such as the background from the machine learning. As described above, if the teaching is performed with the features of the portion not effective for recognition of the abnormal locations such as lesions made closer to each other, various imaged images can be used effectively for learning, and the recognition accuracy can be enhanced.

The second medical image is an image in which the feature according to at least one of the feature information regarding the first medical image is made close to the feature according to the pre-preparation information. That is, whether the similarities are determined as a whole for each parameter in the feature information or the degree of the similarity is determined for each feature information, the conversion to the second medical image is performed according to the contents of the parameter of any of the feature information. Therefore, at least the variation in the image quality related to the parameter can be reduced.

Specifically, in the second medical image, if the feature according to at least one of the feature information regarding the first medical image can be matched with the feature according to the standard feature information, the variation regarding the parameters do not exist, and the types of variation in the image quality can be reduced for the number of matched features. Therefore, the reasons for the erroneous determination in the machine learning can be reduced in this amount, and the learning accuracy of the machine learning with the learning image data that is not sufficient can be enhanced.

The information processing apparatus 1 includes a storage 20 that stores conversion contents of the features corresponding to the difference between the feature information related to the first medical image and the standard feature information. As the image generator, the controller 10 obtains the conversion contents from the storage 20 according to the feature information related to the first medical image and generates the second medical image by applying the conversion contents to the first medical image. As described above, the conversion contents are determined in advance for the feature information in which there is a pattern. Therefore, in the information processing apparatus 1, the variation in the image quality that is not useful for machine learning can be easily reduced. Therefore, the increase in the burden of training the machine learning model related to the recognition of the abnormal locations such as lesions can be suppressed.

Alternatively, in the information processing apparatus 1a, as the image generator, the controller 10 includes the learned model that is trained to perform the following. When the medical image is input, the medical image is made close to the features according to the standard feature information and the medical image is output. That is, by separately preparing and using the learned model that performs preprocessing on the learning data of the machine learning model for recognizing an abnormality such as a lesion, the differences that are not due to the recognition target in the image can be appropriately reduced. With this, the increase in the burden of training the machine learning model related to the recognition of the location of abnormalities such as lesions can be suppressed.

Even in the learning system in which at least some among the configuration as the obtainer, the configuration as the image generator, and the configuration as the learner as described to be performed by the controller 10 are distributed separately, a learned model in which the abnormal locations can be recognized more suitably can be obtained without obtaining sufficient image data for learning.

The learning method of the machine learning model 23 according to the present embodiment includes, an obtaining step that obtains the first medical image, an image generating step that generates the second medical image so that the feature according to the feature information related to the portion other than the recognition target in the first medical image is made closer to the feature according to the standard feature information which is to be the predetermined standard, and the learning step in which the machine learning model 23 is trained to output the recognition result of the recognition target using the second medical image. That is, even if the processes in each step are not performed in a single information processing apparatus 1 or 1a, the machine learning model 23 can be suitably trained with a small amount of image data for learning.

The program 21 according to the present embodiment allows a computer to function as an obtainer that obtains the first medical image, an image generator that generates the second medical image so that the features according to the feature information related to the portion other than the recognition target in the first medical image is made closer to the feature according to the standard feature information which is to be the predetermined standard, and a learner that trains the machine learning model to output the recognition result of the recognition target using the second medical image. As described above, by installing the program 21, the preprocessing of the machine learning is performed by software. Therefore, there is no need for a dedicated information processing apparatus. With this, it is possible to easily prepare data for learning to be learned by the machine learning model 23 used in determining the abnormal locations such as lesions and the training of such machine learning model 23 can be suitably performed even if the amount of learning data is not sufficient.

The present invention is not limited to the above embodiments, and various modifications are possible. For example, according to the present embodiment, the second medical image is generated from the first medical image using the conversion table 22. Alternatively, a conversion formula can be stored instead of the conversion table 22, and the conversion amount can be calculated. Alternatively, the conversion amount can be directly or suitably determined from the difference in the feature amount without preparing a conversion table or a conversion formula in advance.

According to the present embodiment, at least some among the parameters of the feature information of the medical image, especially the image obtaining information are made close to the image quality shown in the standard feature information. However, the embodiments may include the example in which as long as the degree of similarity is increased in the plurality of parameters as a whole, the image quality of some parameters may result in not becoming close to the image quality shown in the standard feature information.

The input of the obtained learned model is not only the medical image and may include additional information such as age and sex. The output of the learned model is not limited to the recognition result, and may be output with other additional information such as the size and the degree of the symptoms.

According to the present embodiment, the conversion process of the image and the processes related to training of the machine learning model 23 are performed in the same information processing apparatus 1 or 1a, but the above processes can be performed in separate information processing apparatuses. That is, in the learning system including two information processing apparatuses, after the image is converted in the first information processing apparatus, the training of the machine learning model 23 can be performed in the second information processing apparatus using the converted image data. Moreover, hardware resources such as cloud servers and rental servers can be used to perform some or all of the processes.

The information processing apparatuses 1 and 1a do not have to be an apparatus dedicated to training the machine learning model 23. The other processes can be performed. For example, the primary process on the first medical images can be performed in the same information processing apparatus. In this case, the medical image data can be sent directly to the generating process of the second medical image without output to the outside.

The parameters and their variables related to the image obtaining information, types of the features related to the image quality and the like according to the above embodiment are not limited to the illustrated examples. The parameters and their variables related to the image obtaining information are to be those that are used to be able to set and identify the imaging apparatus that is able to image the medical image, and the type of feature related to the image quality may include any parameter that is able to represent the image quality quantitatively.

The setting of the standard feature information may be arbitrary. The setting is not limited to the image quality that is obtained in the actual imaging apparatus and may be ideal image quality with which the physician can perform diagnosis smoothly. In this case, not only the original first medical image but also the converted second medical image data itself may be stored and used for diagnosis by the physician.

According to the above description, the storage 20 is provided as an example of a nonvolatile memory such as an HDD, a flash memory or the like which is a computer-readable storage medium that stores the program 21 related to the control of the model learning according to the present embodiment. However, the storage is not limited to the above. As the computer-readable storage medium, a non-volatile memory such as a MRAM, etc., and a portable storage medium, such as a CD-ROM, a DVD disk, etc. may also be used. A carrier wave is also applied as the medium to provide data of the program according to the embodiments through the communication lines.

Other specific configurations, contents and procedures of the processing apparatus, and the like as described in the above embodiments may be suitably changed without leaving the scope of the invention. The scope of the invention includes the scope of the claims and their equivalents.

Although embodiments of the present invention have been described and illustrated in detail, the disclosed embodiments are made for purposes of illustration and example only and not limitation. The scope of the present invention should be interpreted by terms of the appended claims

What is claimed is:

1. A learning apparatus comprising:
   a hardware processor,
   wherein the hardware processor obtains a first medical image,
   wherein the hardware processor generates a second medical image in which a feature according to feature information related to a portion other than a recognition target of the first medical image is made close to the feature according to standard feature information which is to be a predetermined standard, the standard feature information being an average feature information of previously obtained images, and
   wherein the second medical image is used to train a machine learning model.

2. The learning apparatus according to claim 1, wherein the portion other than the recognition target is at least a portion among a range other than a recognition target recognized by the trained machine learning model in the second medical image.

3. The learning apparatus according to claim 1, wherein the feature information includes image obtaining information including at least one among manufacturer information of an imaging apparatus of the first medical image, type information of the imaging apparatus, model information, imaging condition information, imaging facility information, and imaging target information.

4. The learning apparatus according to claim 3, wherein the image obtaining information is associated with a feature related to image quality including at least one of the following, sharpness, contrast, noise, density, tone, and resolution.

5. The learning apparatus according to claim 1, wherein the first medical image is any or a combination of two or more of the following, an X-ray imaged image, an ultrasound imaged image, a nuclear magnetic resonance imaged image, and positron emission tomographic image.

6. The learning apparatus according to claim 1, wherein the second medical image is an image in which a feature according to at least one item in the feature information related to the first medical image is made close to the feature according to the standard feature information.

7. The learning apparatus according to claim 6, wherein the second medical image is an image in which a feature according to at least one item in the feature information related to the first medical image is matched with the feature according to the standard feature information.

8. The learning apparatus according to claim 1, further comprising: a storage that stores conversion contents of the feature corresponding to a difference between the feature information related to the first medical image and the standard feature information,
wherein the hardware processor generates the second medical image by obtaining the conversion contents from the storage according to the feature information and applying the conversion contents to the first medical image.

9. The learning apparatus according to claim 1, wherein the hardware processor includes a learned model which is trained to output a medical image in which the medical image is made close to a feature according to the standard feature information in response to input of the medical image.

10. The learning apparatus according to claim 1, wherein the hardware processor generates the second medical image by applying a conversion to the first medical image so that the feature according to feature information related to the portion other than the recognition target of the first medical image is made close to the feature according to the standard feature information.

11. The learning apparatus according to claim 1, wherein the previously obtained images from which the average feature information is determined are obtained in a basic setting of one or more imaging apparatus.

12. A learning system comprising:
a hardware processor,
wherein the hardware processor obtains a first medical image,
wherein the hardware processor generates a second medical image in which a feature according to feature information related to a portion other than a recognition target of the first medical image is made close to the feature according to standard feature information which is to be a predetermined standard, the standard feature information being an average feature information of previously obtained images, and
wherein the hardware processor uses the second medical image to train a machine learning model.

13. A learning method of a machine learning model comprising:
obtaining a first medical image;
generating a second medical image in which a feature according to feature information related to a portion other than a recognition target of the first medical image is made close to the feature according to standard feature information which is to be a predetermined standard, the standard feature information being an average feature information of previously obtained images, and
training a machine learning model using the second medical image.

14. A non-transitory computer-readable storage medium storing a program causing a computer to perform:
obtaining a first medical image;
generating a second medical image in which a feature according to feature information related to a portion other than a recognition target of the first medical image is made close to the feature according to standard feature information which is to be a predetermined standard, the standard feature information being an average feature information of previously obtained images, and
training a machine learning model using the second medical image.

* * * * *